(12) United States Patent
Stupp et al.

(10) Patent No.: US 7,452,679 B2
(45) Date of Patent: Nov. 18, 2008

(54) BRANCHED PEPTIDE AMPHIPHILES, RELATED EPITOPE COMPOUNDS AND SELF ASSEMBLED STRUCTURES THEREOF

(75) Inventors: Samuel I. Stupp, Chicago, IL (US); Mustafa O. Guler, Evanston, IL (US)

(73) Assignee: Northwestern University, Evanston, IL (US)

( * ) Notice: Subject to any disclaimer, the term of this patent is extended or adjusted under 35 U.S.C. 154(b) by 182 days.

(21) Appl. No.: 11/005,314

(22) Filed: Dec. 6, 2004

(65) Prior Publication Data

US 2005/0208589 A1    Sep. 22, 2005

Related U.S. Application Data

(60) Provisional application No. 60/527,442, filed on Dec. 5, 2003.

(51) Int. Cl.
*G01N 33/53* (2006.01)
*G01N 33/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. .................. 435/7.1; 436/86; 530/330
(58) Field of Classification Search .............. None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,130,123 A | 7/1992 | Reynolds et al. | |
| 5,208,111 A | 5/1993 | Decher et al. | |
| 5,670,483 A | 9/1997 | Zhang et al. | |
| 5,733,868 A | 3/1998 | Peterson et al. | |
| 5,843,780 A | 12/1998 | Thomson | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,391,297 B1 | 5/2002 | Halvorsen | |
| 6,444,723 B1 | 9/2002 | Kline | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0059906 A1 | 3/2003 | Hubbell et al. | |
| 2003/0092672 A1 | 5/2003 | Darcy et al. | |
| 2003/0176335 A1 | 9/2003 | Zhang et al. | |
| 2004/0001893 A1 | 1/2004 | Stupp et al. | |
| 2004/0018961 A1 | 1/2004 | Stupp et al. | |
| 2004/0022718 A1 | 2/2004 | Stupp et al. | |
| 2004/0258726 A1 | 12/2004 | Stupp et al. | |
| 2005/0208589 A1 | 9/2005 | Stupp et al. | |
| 2005/0209145 A1 | 9/2005 | Stupp et al. | |
| 2005/0214257 A1 | 9/2005 | Zhao et al. | |
| 2005/0272662 A1 | 12/2005 | Stupp et al. | |
| 2006/0149036 A1 | 7/2006 | Stupp et al. | |
| 2006/0247165 A1* | 11/2006 | Stupp et al. .............. 514/12 |

FOREIGN PATENT DOCUMENTS

| | | |
|---|---|---|
| JP | 03099096 A | 4/1991 |
| WO | WO 97/14713 A1 | 4/1997 |
| WO | WO 97/20639 A1 | 6/1997 |
| WO | WO 98/07752 A1 | 2/1998 |
| WO | 99/36107 | 7/1999 |
| WO | WO 00/13710 | 3/2000 |
| WO | 00/45831 A1 | 8/2000 |
| WO | WO 00/44808 A1 | 8/2000 |
| WO | WO 00/52145 A2 | 9/2000 |

(Continued)

OTHER PUBLICATIONS

Nomizu et al. Multimeric Forms of Tyr-lle-Gly-Ser-Arg Peptide Enhnace the Inhibition of Tumor Growth and Metastasis. Advances in Brief. Cancer Research. 1993. vol. 53, pp. 3459-3461.*
AccessScience Search Results. Amphiphile. http://www.access-science.com/search/asearch?location=titlestext&newSearch=1&pubpriv=private&categories=dictionary&categval=dictionary&text=amphiphile, accessed online May 7, 2007.*
Wang-Lin-Fa. Epitope Identification and Discovery Using Phase Display Libraries: Applications in Vacine Development and Diagnostics. Current Drug Targets, 2004, vol. 5, No. 1, pp. 1-15.
Donners et al. Growth factor binding self-assembling nanofiber networks for tissue regeneration. Mar. 28-Apr. 1, 2004. Abstracts of Papers, 227th ACS National Meeting, Anaheim, CA, American Chemical Society. BIOT-023.

(Continued)

*Primary Examiner*—Cecilia J Tsang
*Assistant Examiner*—Marcela M Cordero Garcia

(57) ABSTRACT

Branched peptide amphiphilic compounds incorporating one or residues providing a pendant amino group for coupling one or more epitope sequences thereto, such compounds and related compositions for enhanced epitope presentation.

21 Claims, 6 Drawing Sheets

FOREIGN PATENT DOCUMENTS

| WO | WO 00/64481 | 11/2000 |
|---|---|---|
| WO | WO 01/00650 A1 | 1/2001 |
| WO | WO 03/040336 | 5/2003 |
| WO | WO 03/054146 A2 | 7/2003 |
| WO | WO 02/062969 | 8/2003 |
| WO | WO 03/070749 | 8/2003 |
| WO | WO 03/084980 A2 | 10/2003 |
| WO | WO 03/090255 A2 | 10/2003 |
| WO | WO 2004/003561 A1 | 1/2004 |
| WO | WO 2004/018628 A2 | 3/2004 |
| WO | WO 2004/024778 A2 | 3/2004 |
| WO | WO 2004/046167 A2 | 6/2004 |
| WO | WO 2004/072104 A2 | 8/2004 |
| WO | WO 2004/106359 A2 | 12/2004 |
| WO | WO 2005/003292 A2 | 1/2005 |
| WO | WO 2005/056039 A1 | 6/2005 |
| WO | WO 2005/056576 | 6/2005 |
| WO | WO 2006/096614 A2 | 9/2006 |

OTHER PUBLICATIONS

Anthony et al. Self-assembling nanofiber matrix for bone regeneration. Mar. 28, Apr. 1, 2004, Abstracts of Papers, 227th ACS National Meeting, Anaheim, CA, American Chemical Soxiety. BIOT-340.

Anthony. Injectable Biomaterials for Bone Tissue Engineering. http://www.nuance.northwestern.edu/downloads/Anthony%20Murphy%20Report%20Spring%202003.pdf (Spring 2003) Accessed online Apr. 28, 2005. pp. 1-12. See entire document, e.g., pp. 3-7 and figures 102.

Guler, Mustafa, O. et al., "Presentation and Recognition of Biotin on Nanofibers Formed by Branched Peptide Amphiphiles", Nano Letters 2005, vol. 5, No. 2, pp. 249-252. Copyright 2005 American Chemical Society, Published on Web Dec. 29, 2004.

Hartgerink, Jeffrey D., et al., "Self-Assembly and Mineralization of Peptide-Amphiphile Nanofibers", www.sciencemag.org, Nov. 23, 21. vol. 294, pp. 1684-1688.

Silva, Gabriel, A., et al., "Selective Differentiation of Neural Progenitor Cells by High-Epitope Density Nanofibers", www.sciencemag.org, Feb. 27, 2004, vol. 303, pp. 1352-1355.

Hartgerink, Jeffrey D., et al., "Peptide-amphiphile nanofibers: A versatile scaffold for the preparation of self-assembling materials", PNAS, Apr. 16, 2002, vol. 99, No. 8, pp. 5133-8138 (www.pnas.org/cgi/dol/10.1073/pnas.072699999).

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." The Journal of Biological Chemistry. vol. 267, No. 20, pp. 14118-14121.

Margomenou-Leonidopoulou, G. 1994. "Thermotropic Mesophases of Ionic Amphiphiles. II. Ionic Amphiphiles in Aqueous Media." Journal of Thermal Analysis. vol. 42, pp. 1041-1061.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Goveas, J. L. and S. T. Milner. 1997. "Dynamics of the Lamellar—Cylindrical Transition in Weakly Segregated Diblock Copolymer Melts." Macromolecules. vol. 30, No. 9, pp. 2605-2612.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Fernandez, A., M. A. Alsina, I. Haro, R. Galantai, and F. Reig. 1998. "Synthesis and Physicochemical Characterization of Cyclic Laminin Related Peptides." Langmuir. vol. 14, No. 13, pp. 3625-3630.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." Chem. Commun. pp. 1687-1688.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann: 2001. "Selective Adhesion of Endothelial Cells to Artificial Membranes with a Synthetic RGD-Lipopeptide." Chem. Eur. J. vol. 7, No. 5, pp. 1095-1101.

Blight, Andrew R. Nov. 2002. "Miracles and Molecules—Progress in Spinal Cord Repair." Nature Neuroscience Supplement. vol. 5, pp. 1051-1054.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Nluvis Perez, and Michael J. Hannon. 2002. "Flow Oriented Linear Dichroism to Probe Protein Orientation in Membrane Environments." Phys. Chem. Chem. Phys. vol. 4, pp. 4051-4057.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fermentans." Eur. J. Biochem. vol. 270, pp. 3271-3279.

Czeisler, C., V. M. Tysseling-Mattiace, G. A. Silva, S. I. Stupp, and J. A. Kessler. 2003. "Behavioral Improvement and Increased Survival Rate after Treatment with a Self Assembling Gel In a Rat Model of Spinal Cord Injury." 2003 Abstract Viewer/Itinerary Planner. Program No. 245.22. Washington, DC: Society for Neuroscience. Printed Feb. 5, 2007. p. 1. http://sfn.scholarone.com/itin2003/main.html?new_page_id=126&abstract_id=1544 . . . .

Schmidt, Christine E. and Jennie Baier Leach. 2003. "Neural Tissue Engineering: Strategies for Repair and Regeneration." Annu. Rev. Biomed. Eng. vol. 5, pp. 293-347.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." Acta Biomaterialia. vol. 1, pp. 387-397.

Hoke, Ahmet. Aug. 2006. "Mechanisms of Disease: What Factors Limit the Success of Peripheral Nerve Regeneration in Humans?" Nature Clinical Practice Neurology. vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

The LabRat.com. 2007, updated. Hank's Buffered Salt Solution (HBSS) Recipe. http://www.thelabrat.com/protocolsHanks.shtml. Printed Jan. 19, 2007. pp. 1-2.

U.S. Appl. No. 11/337,316, filed Jan. 23, 2006, Stupp et al.

Brown, Walter E. Dec. 15, 1962. "Octacalcium Phosphate and Hydroxyapatite." Nature. vol. 196, pp. 1048-1050.

Liang, W. Y. and A. D. Yoffe. Jan. 8, 1968. "Transmission Spectra of ZnO Single Crystals." Physical Review Letters. vol. 20, No. 2, pp. 59-62.

Greenfield, Norma and Gerald D. Frasman. Oct. 1969. "Computed Circular Dichroism Spectra for the Evaluation of Protein Conformation." Biochemistry. vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the Escherichia coli Outer Membrane." Eur. J. Biochem. vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." Journal of the American Chemical Society. vol. 98, No. 12, pp. 3470-3473.

Jacobson, Bruce S. and Daniel Branton. Jan. 21, 1977. "Plasma Membrane: Rapid Isolation and Exposure of the Cytosplasmic Surface by Use of Positively Charged Beads." Science. vol. 195, No. 4275, pp. 302-304.

Biesecker, G., J. Ieuan Harris, J. C. Thierry, J. E. Walker, and A. J. Wonacott. Mar. 24, 1977. *Nature.* vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society.* vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International.* vol. 27, No. 1, pp. 75-82.

Richardson, P. M., U. M. McGuiness, and A. J. Aguayo. Mar. 20, 1980. "Axons from CNS Neurones Regenerate into PNS Grafts." *Nature.* vol. 284, pp. 264-265.

Lim, Franklin and Anthony M. Sun. Nov. 21, 1980. "Microencapsulated Islets as Bioartificial Endocrine Pancreas." *Science.* vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters.* vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry.* vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science.* vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology.* vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature.* vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol.* vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta.* vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." *Chemistry Letters.* No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America.* vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters.* vol. 206, No. 2, pp. 262-266.

Mann, Stephen, John P. Hannington, and R. J. P. Williams. Dec. 11, 1986. "Phospholipid Vesicles as a Model System for Biomineralization." *Nature.* vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry.* vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research.* vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology.* vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology.* vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy.* New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research.* No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology.* vol. 107, pp. 743-751.

Cardin, Alan D. and H. J. R. Weintraub. Jan./Feb. 1989. "Molecular Modeling of Protein-Glycosaminoglycan Interactions." *Arteriosclerosis.* vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery.* vol. 71-B, No. 2, pp. 213-216.

Friedmann, Theodore. Jun. 16, 1989. "Progress Toward Human Gene Therapy." *Science.* vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America.* vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters.* vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual.* 2$^{nd}$ ed. New York: Cold Spring Harbor Laboratory Press. pp. 16.9-16.15.

Veis, A. 1989. "Biochemical Studies of Vertebrate Tooth Mineralization." *Biomineralization.* S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature.* vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery.* vol. 24, No. 1, pp. 17-23.

Van de Pol, Frans C. M. Dec. 1990. "Thin-Film ZnO—Properties and Applications." *Ceramic Bulletin.* vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta.* vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research.* vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research.* vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry.* vol. 56, No. 22, pp. 14353-14358.

Harris, Robin, Editor. 1991. *Electron Microscopy in Biology: A Practical Approach.* New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society.* vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Ångstroms to Microns." *The FASEB Journal*. vol. 6, pp. 879-885.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl.* vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research*. vol. 26, pp. 169-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Ainsotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Ross-Murphy, S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater*. vol. 5, No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi, L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J*. vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research*. vol. 28, pp. 909-917.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials*. vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*. vol. 18, pp. 1417-1426.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falani, Guiseppe, Shira Albeck, Steve Weiner, and Lia Addadi. Jan. 5, 1996. "Control of Aragonite or Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry*. vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mulluse-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J*. vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl. Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Ratner, Buddy D., Allan S. Hoffman, Frederick J. Schoen, and Jack E. Lemons, Editors. 1996. *Biomaterials Science: An Introduction to Materials in Medicine*. San Diego, CA: Academic Press.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids*. vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature*. vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem*. vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudmund Skjåk-Bræk, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function in Vitro Along Different Time Lines." *Journal of Biomedical Materials Research*. vol. 36, pp. 167-180.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells In Vitro." *Journal of Cellular Biochemistry*. vol. 64, pp. 295-312.

Nehrer, Stefan, Howard A. Breinan, Arun Ramappa, Sonya Shortkroff, Gretchen Young, Tom Minas, Clement B. Sledge, Ionnis V. Yannas, and Myron Spector. 1997. "Canine Chondrocytes Seeded in Type I and Type II Collagen Implants Investigated In Vitro." *Journal of Biomedical Materials Research (Appl. Biomater.)*. vol. 38, pp. 95-104.

Mann, Stephen. 1997. "Biomineralization: The Form(id)able Part of Bioinorganic Chemistry!" *J. Chem. Soc., Dalton Trans*. pp. 3953-3961.

Norrby, Klas. 1997. "Angiogenesis: New Aspects Relating to Its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexgonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem*. vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Desposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Fields, Gregg B., Janelle L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science)*. vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J*. vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valylvaline Bolaamphiphiles." *Chem. Comm*. pp. 1791-1792.

Li, Panjian and Paul Ducheyne. 1998. "Quasi-Biological Apatite Film Induced by Titanium in a Simulated Body Fluid." *Journal of Biomedical Materials Research*. vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research*. vol. 40, pp. 324-335.

Tsui, Y. C., C. Doyle, and T. W. Clyne. 1998. "Plasma Sprayed Hydroxyapatite Coatings on Titanium Substrates Part 2: Optimasation of Coating Properties." *Biomaterials*. vol. 19, pp. 2031-2043.

Weiner, S. and H. D. Wagner. 1998. "The Material Bone: Structure-Mechanical Function Relations." *Annu. Rev. Mater. Sci*. vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research*. vol. 41, pp. 227-236.

Wheeler, Donna L., David L. Chamberland, John M. Schmitt, David C. Buck, John H. Brekke, Jeffrey O. Hollinger, S.-P. Joh, and K.-W. Sub. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.)*. vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research*. vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir*. vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society*. vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society*. vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry*. vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science*. vol. 283, pp. 523-526.

Won, You-Yeon, H. Ted Davis, and Frank S. Bates. Feb. 12, 1999. "Giant Wormlike Rubber Micelles." *Science*. vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg*. vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering*. vol. 121, pp. 73-78.

Cao, H., Y. G. Zao, S. T. Ho, E. W. Seelig, Q. H. Wang, and R. P. H. Chang. Mar. 15, 1999. "Random Laser Action in Semiconductor Powder." *Physical Review Letters*. vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature*. vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science*. vol. 284, pp. 489-493.

Hahn, Jungseok and Stephen E. Webber. Apr. 1999. "Modification of Surfaces by Covalent Attachment of Polymer Micelles." *Macromolecular Symposia*. vol. 139, pp. 39-47.

Liu, Yi, Duckyyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience*. vol. 19, No. 11, pp. 4370-4387.

Mehler, Mark F. and John A. Kessler. Jul. 1999. "Progenitor Cell Biology: Implications for Neural Regeneration." *Arch. Neurol*. vol. 56, pp. 780-784.

Tirrell, M. Oct. 27, 1999. "Biofunctionalization of Surfaces with Peptide Amphiphiles." *AVS: Science & Technology*. Invited Paper B1-WeM7.

McDonald, John W., Xiao-Zhong, Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine*. vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater*. vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin*. vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery*. vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine*. vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J*. vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physiol. Endocrinol. Metab*. vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir*. vol. 15, No. 16, pp. 5212-5218.

Fields, Gregg B. 1999. "Induction of Protein-like Molecular Architecture by Self-Assembly Processes." *Bioorganic & Medicinal Chemistry*. vol. 7, pp. 75-81.

Haynes, Andrew J., Wei-Qun Huang, Jamie Mallah, Dajun Yang, Marc E. Lippman, and Lu-Yuan Li, 1999. "Angiopoietin-1 and Its Receptor Tie-2 Participate in the Regulation of Capillary-like Tubule Formation and Survival of Endothelial Cells." *Microvascular Research*. vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research*. vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials*. vol. 20, pp. 809-816.

Lee, Kevin J. and Thomas M. Jessell. 1999. "The Specification of Dorsal Cell Fates in the Vertebrate Central Nervous System." *Annual Review of Neuroscience*. vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir*. vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth*. vol. 206, pp. 308-321.

Miyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials*. vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials*. vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science*. vol. 284, pp. 143-147.

Rezania, Alireza, Robert Johnson, Anthony R. Lefkow, and Kevin E. Healy. 1999. "Bioactivation of Metal Oxide Surfaces. I. Surface Characterization and Cell Response." *Langmuir*. vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials*. vol. 20, pp. 45-53.

Scheuse, Jason C. and Jeffrey A. Hubbell. 1999. "Cross-Linking Exogenous Bifunctional Peptides into Fibrin Gels with Factor XIIIa." *Bioconjugate Chem*. vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine*. vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research*. vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine*. vol. 10, pp. 401-409.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry*. vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling*. vol. 6, pp. 35-47.

Martinez, J. S., G. P. Zhang, P. D. Holt, H.-T. Jung, C. J. Carrano, M. G. Haygood, and Alison Butler. Feb. 18, 2000. "Self-Assembling Amphiphilic Siderophores from Marine Bacteria." *Science*. vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry*. vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters*. vol. 76, No. 21, pp. 2997-2999.

Marler, Jennifer J., Amrita Guba, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery*. vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America.* vol. 97, No. 12, pp. 6728-6733.

Whaley, Sanda R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature.* vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry.* vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant:" *Investigative Ophthalmology & Visual Science.* vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell.* vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters.* vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America.* vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science.* vol. 9, pp. 1095-1105.

Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society.* vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir.* vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology.* vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules.* vol. 1, No. 4, pp. 752-756.

Bourel, Line, Olivier Carion, Hélène Gras-Masse, and Oleg Melnyk. 2000. "The Deprotection of Lys(Mtt) Revisited." *Journal of Peptide Science.* vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules.* vol. 1, No. 4, pp. 627-631.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun.* pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research.* vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research.* vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research.* vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains." *Biopolymers.* vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artificial Enzyme." *Colloids and Surfaces A: Physicochemical and Engineering Aspects.* vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel β-Sheet Network." *Biochimica et Biophysica Acta.* vol. 1475, pp. 346-352.

Langer, Robert. 2000. "Biomaterials in Drug Delivery and Tissue Engineering: One Laboratory's Experience." *Accounts of Chemical Research.* vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med.* vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials.* vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials.* vol. 21, pp. 1121-1127.

Ponticello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research.* vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research.* vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release.* vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release.* vol. 65, pp. 389-402.

Thareja, R. K. and A. Mitra. 2000. "Random Laser Action in ZnO." *Appl. Phys.* vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique.* vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research.* vol. 49, pp. 345-352.

Yamada, Norihiko and Katsuhiko Ariga. 2000. "Formation of α-Sheet Assemblage with a View to Developing an Amyloid Model." *Synlett.* vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science.* vol. 5, pp. 132-143.

Yu, Huaoran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science.* vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research.* vol. 59, pp. 312-320.

Orlic, Donald, Jan Kajstura, Stefano Chimenti, Igor Jakonuk, Stacie M. Anderson, Baosheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature.* vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation.* vol. 81, No. 4, pp. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res.* vol. 16, No. 5, pp. 1508-1519.

Rabchevsky, Alexander G. and George M. Smith. May 2001. "Therapeutic Interventions Following Mammalian Spinal Cord Injury." *Arch. Neurol.* vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science.* vol. 292, pp. 1897-1899.

Lee, Kuen Yong and David J. Mooney. Jul. 2001. "Hydrogels for Tissue Engineering." *Chemical Reviews.* vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America.* vol. 98, No. 21, pp. 11857-11862.

Richardson, Thomas P., Martin C. Peters, Alessandra B. Ennett, and David J. Mooney. Nov. 2001. "Polymeric System for Dual Growth Factor Delivery." *Nature Biotechnology.* vol. 19, pp. 1029-1034.

Mathew, Mathai and Shozo Takagi. Nov.-Dec. 2001. "Structures of Biological Minerals in Dental Research." *Journal of Research of the National Institute of Standards and Technology.* vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research.* vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine.* vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir.* vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science.* vol. 36, pp. 3253-3260.

Chang, John C., Gregory J. Brewer, and Bruce C. Wheeler. 2001. "Modulation of Neural Network Activity by Patterning." *Biosensors & Bioelectronics.* vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Choudrocyte/Alginate Constructs in the Shape of Facial Implants." *Journal of Biomedical Materials Research.* vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal.* vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir.* vol. 17, No. 17, pp. 5352-5360.

Hoess, Ronald H. 2001. "Protein Design and Phage Display." *Chemical Reviews.* vol. 101, No. 10, pp. 3205-3218.

Huang, Eric J. and Louis F. Reichardt. 2001. "Neurotrophins: Roles in Neuronal Development and Function." *Annual Review of Neuroscience.* vol. 24, pp. 677-736.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials.* vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nanocomposite Synthesized in Vitro and Its Biological Reaction in Vivo." *Biomaterials.* vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research.* vol. 57, pp. 327-335.

Look, D. C. 2001. "Recent Advances in ZnO Materials and Devices." *Materials Science and Engineering.* vol. B80, pp. 383-387.

Matsui, Hiroshi, and Gary E. Douberly, Jr. 2001. "Organization of Peptide Nanotubes into Macroscopic Bundles." *Langmuir.* vol. 17, No. 25, pp. 7918-7922.

Neet, K. E. and R. B. Campenot. 2001. "Receptor Binding, Internalization, and Retrograde Transport of Neurotrophic Factors." *CMLS, Cell Mol. Life Sci.* vol. 58, pp. 1021-1035.

Otsuka, Hidenori, Yukio Nagasaki, and Kazunori Kataoka. 2001. "Self-Assembly of Poly(ethylene glycol) -based Block Copolymers for Biomedical Applications." *Current Opinion in Colloid & Interface Science.* vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the American Chemical Society.* vol. 123, No. 25, pp. 5947-5955, S1-S16.

Socrates, George. 2001. *Infrared and Raman Characteristic Group Frequencies: Tables and Charts.* Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir.* vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research.* vol. 57, pp. 441-448.

Tanihara, Masao, Yasuo Suzuki, Eriko Yamamoto, Atsushi Noguchi, and Tutaka Mizushima. 2001. "Sustained Release of Basic Fibroblast Growth Factor and Angiogenesis in a Novel Covalently Crosslinked Gel of Heparin and Alginate." *Journal of Biomedical Materials Research.* vol. 56, pp. 216-221.

Torchilin, Vladimir P. 2001. "Structure and Design of Polymeric Surfactant-Based Drug Delivery Systems." *Journal of Controlled Release.* vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters.* vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society.* vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-β Induction of Smooth Muscle Cell Phenotype Requires Transcriptional and Post-transcriptional Control of Serum Response Factor." *The Journal of Biological Chemistry.* vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal.* vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials*. vol. 14, No. 3, pp. 198-203.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America*. vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Vauthey, Sylvain, Steve Santuso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Busqué, Félix, Stephanie A. Hopkins, and Joseph P. Konopelski. 2002. "Progress Toward a Peptidomimetic of Laminin-Derived Pentapeptide VIGSR: Synthesis of the Unique Tricyclic Core Structure." *J. Org. Chem.* vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn.* vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem.* vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir*. vol. 18, No. 1, pp. 252-258.

Issac, Roy and Jean Chmielewski. 2002. "Approaching Exponential Growth with a Self-Replicating Peptide." *Journal of the American Chemical Society*. vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma*. vol. 19, No. 2, pp. 191-203.

Kruger, Ryan G., Patrick Dostal, and Dewey G. McCafferty. 2002. "An Economical and Preparative Orthogonal Solid Phase Synthesis of Fluroescein and Rhodamine Derivatized Peptides: FRET Substrates for the *Staphylococcus aureus* Sortase SrtA Transpeptidase Reaction." *Chem. Commun.* pp. 2092-2093.

Lauer, L., A. Vogt, C. K. Yeung, W. Knoll, and A. Offenhähausser. 2002. "Electrophysiological Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters*. vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dentritic Poly(L-lysine)." *Bioconjugate Chem.* vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rowley, Jon A. and David J. Mooney. 2002. "Alginate Type and RGD Density Control Myoblast Phenotype." *Journal of Biomedical Materials Research*. vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science*. vol. 7, pp. 262-266.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics*. vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667.

Young, Wise. 2002. "Spinal Cord Contusion Models." *Progress in Brain Research*. vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Memetics of Collagenous Extracellular Matrices." *Nature Biotechnology*. vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Cheng, Hongwei, Wei Jiang, Frank M. Phillips, Rex C. Haydon, Ying Peng, Lan Zhou, Hue H. Luu, Naili Au, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery*. vol. 85-A, No. 8, pp. 1544-1552, 141.

Pavlov, Georges, Stéphanie Finet, Karine Tatarenko, Evgueniya Korneeva, and Christine Ebel. 2003. "Conformation of Heparin Studied with Macromolecular Hydrodynamic Methods and X-ray Scattering." *Eur. Biophys. J*. vol. 32, pp. 437-449.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery*. vol. 85-A, No. 10, pp. 1927-1935.

Zhang, Shuguang. Oct. 2003. "Fabrication of Novel Biomaterials Through Molecular Self-Assembly." *Nature Biotechnology*. vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernando Albericio. 2003. "Solid-Phase Synthesis of C-Terminal Modified Peptides." *Biopolymers (Peptide Science)*. vol. 71, pp. 454-477.

Boontheekul, Tanyarut and David J. Mooney. 2003. "Protein-Based Signaling Systems in Tissue Engineering." *Current Opinion in Biotechnology*. vol. 14, pp. 559-565.

Fauza, Dario O. 2003. "Tissue Engineering: Current State of Clinical Application." *Current Opinion in Pediatrics*. vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Füredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishiharu, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society*. vol. 125, No. 24, pp. 7146-7147.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed*. vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8788-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura Sachiko, Shinobu Uemura, and Hisakazu Mihara. 2004. "Fabrication of Nanofibers with Uniform Morphology by Self-Assembly of Designed Peptides." *Chem. Eur. J*. vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Sayle, Roger. Printed Nov. 9, 2005. "Physiological Ionization and pKa Prediction." http://www.daylight.com/meetings/emug00/Sayle/pkapredict.html. pp. 1-13.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Copping, Aaron M. and Vanda R. G. Pond. Dec. 9, 1950. "Folic Acid as a Growth-Factor for the Rat." Nature. No. 4232, p. 993.

Mulloy, Barbara and Mark J. Forster. 2000. "Conformation and Dynamics of Heparin and Heparan Sulfate." Glycobiology. vol. 10, No. 11, pp. 1147-1156.

Bruggemann, Holger, Sebastian Baumer, Wolfgang Florian Fricke, Arnim Wiezer, Heiko Liesegang, Iwona Decker, Christina Herzberg, Rosa Martinez-Arias, Rainer Merkl, Anke Henne, and Gerhard Gottschalk. Feb. 4, 2003. "The Genome Sequence of *Clostridium tetani*, the Causative Agent of Tetanus Disease." PNAS. vol. 100, No. 3, pp. 1316-1321.

Invitrogen. Printed Jan. 22, 2008. "Dulbecco's Modified Eagle Medium (D-MEM) (1X) Liquid (High Glucose)." http://www.invitrogen.com/content.cfm?pageId=95&fuseaction=MediaForm.dsp_mediaForm&productId . . . .

Uniprot entry for Q899Z6. Printed Mar. 14, 2008. http://www.pir.uniprot.org/cgi-bin/upEntry?id=Q899Z6_CLOTE. 3 pages.

Jackowski, Andre. 1995. "Neural Injury Repair: Hope for the Future as Barriers to Effective CNS Regeneration Become Clearer." J. Neurosurg. vol. 9, pp. 303-317.

Knake, Rene, Amir W. Fahmi, Syed A. M. Tofail, Jason Clohessy, Miroslav Milhov, and Vincent J. Cunnane. 2005. "Electrochemical Nucleation of Gold Nanoparticles in a Polymer Film at a Liquid-Liquid Interface." Langmuir. vol. 21, No. 3, pp. 1001-1008.

Jin, Young-Gu and K. J. Chang. Feb. 26, 2001. "Mechanism for the Enhanced Diffusion of Charged Oxygen Ions in SiO2." Physical Review Letters. vol. 86, No. 9, pp. 1793-1796.

Matsui, Hiroshi and Robert MacCuspie. Dec. 2001. "Metalloporphyrin Nanotube Fabrication Using Peptide Nanotubes as Templates." Nano Letters. vol. 1, No. 12, pp. 671-675.

Irvine, Darrell J. and Anne M. Mayes. 2001. "Nanoscale Clustering of RGD Peptides at Surfaces Using Comb Polymers. 1. Synthesis and Characterization of Comb Thin Films." Biomacromolecules. vol. 2, No. 1, pp. 85-94.

Matsui, Hiroshi, Precila Porrata, and Gary E. Douberly, Jr. 2001. "Protein Tubule Immobilization on Self-Assembled Monolayers on Au Substrates." Nano Letters. vol. 1, No. 9, pp. 461-464.

Slocik, Joseph M., Joshua T. Moore, and David W. Wright. Mar. 2002. Monoclonal Antibody Recognition of Histidine-Rich Peptide Encapsulated Nanoclusters. Nano Letters. vol. 2, No. 3, pp. 169-173.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." Langmuir. vol. 18, No. 8, pp. 3332-3335.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." Nano Letters. vol. 2, No. 6, pp. 583-587.

\* cited by examiner

```
    K
     K--LL--CCCC-(K)--C16
    K
```

6

```
DOTA--KG-RGDS-K
               K--LLL--AAA-(K)--C16
               K
```

7

SEQUENCE LISTING

```
<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro His Ser Arg Asn
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Lys Val Ala Val
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile Gly Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Gly Arg Gly Asp Ser Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Leu Leu Leu Ala Ala Ala Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gly Asp Ser Lys
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 8

Ser Leu Ser Leu
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ala Ala
1

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Gly or Leu

<400> SEQUENCE: 10

Lys Xaa Xaa Xaa Ala Ala Ala Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Leu or Lys

<400> SEQUENCE: 11

Lys Xaa Xaa Xaa Ala Ala Ala Lys
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Asp Gly Arg
1

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Ala Ala Ala Leu Leu Leu Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala Leu Leu Leu Lys Lys
1               5
```

US 7,452,679 B2

BRANCHED PEPTIDE AMPHIPHILES, RELATED EPITOPE COMPOUNDS AND SELF ASSEMBLED STRUCTURES THEREOF

This application claims priority benefit from application Ser. No. 60/527,442 filed Dec. 5, 2003, the entirety of which is incorporated herein by reference.

The United States government has certain rights to this invention pursuant to Grand No. DE-FG02-00ER54810 from the Department of Energy to Northwestern University.

BACKGROUND OF THE INVENTION

Molecular recognition among ligands and receptors in biology requires appropriate presentation of epitopes. Cellular adhesion ligands in extracellular matrix play a critical role in cell adhesion and attachment, which affect cell proliferation, differentiation and maintaining regular metabolic activities. Recently, there has been great interest in designing scaffolds that mimic cellular structures with artificial epitopes, in order to trigger biological events important in regenerative medicine or targeted chemotherapy. Differences in cellular response have been reported with changes in distribution and structural presentation of the signals on these artificial cell scaffolds. For, example, varying the nanoscale separation between cell adhesion ligands has been found to improve the recognition of signals and subsequent proliferation of the cells. Among the various methodologies used to synthesize biomaterials, self-assembly is a particularly attractive tool to create scaffolds from solutions of molecules that can encapsulate cells and assemble in situ.

SUMMARY OF THE INVENTION

In light of the foregoing, it is an object of the present invention to provide a molecular architecture for delivery and presentation of biologically active epitopes, thereby addressing various concerns in the art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object to the present invention to provide compounds and related compositions capable of self-assembly for structural presentation of a wide range of bioactive epitopes.

It can be another object of the present invention to provide molecular structures comprising compounds enhancing epitope presentation and corresponding signal recognition.

It can be another object of the present invention to provide a wide range of amphiphilic peptide compounds having a three-dimensional structure for separation of epitopes/cell adhesion ligands, such compounds capable of self-assembly, under physiological conditions, for presentation and distribution of such epitopes/cell adhesion ligands.

Other objects, features, benefits and advantages of the present invention will be apparent from this summary and certain embodiments described below, and will be readily apparent to those skilled in the art having knowledge of various amphiphilic compounds, self-assembly techniques and peptide synthesis. Such objects, features, benefits and advantages will be apparent from the above as taken into conjunction with the accompanying examples, data, figures and all reasonable inferences to be drawn therefrom, alone or with consideration of the references incorporated herein.

In part, the present invention can comprise a non-linear peptide amphiphile compound. Such a compound comprises a peptide component comprising at least one amino acid residue comprising a pendant amino group. The amino group can be coupled to or bonded directly with a component non-linear width the length or longitudinal axis of the peptide component. Providing such a compound amphiphilic character, the peptide component is coupled to or bonded directly with a hydrophobic component. As discussed more fully below, the aforementioned amino acid residue can be of a naturally or non-naturally occurring amino acid. Likewise, the pendant amino group can be derived from another functional group before or after incorporation into the peptide component. Further, as would be understood by those skilled in the art, such pendency can comprise any group functionally capable of coupling or bonding directly to another component so as to provide the compound a branched or non-linear configuration. Regardless, in certain embodiments, such a residue can be of one of several naturally-occurring amino acids, including but not limited to lysine.

Incorporation of at least two such residues can be used to couple to the peptide component one or more bioactive epitope sequences. Such sequences include but are not limited to those provided in co-pending application Ser. No. 10/368,517 filed Feb. 18, 2003 (International publication no. WO 03/070749) and in co-pending application entitled, "Self Assembling Peptide Amphiphiles and Related Methods for Growth Factor Delivery" filed concurrently herewith on Dec. 6, 2004, each of which is incorporated herein by reference in its entirety. Accordingly, such sequences can be selected from known and/or available cellular adhesion ligands relating to e.g., cell proliferation, differentiation and/or metabolism, biomimetic variations thereof and/or binding sequences interactive with a range of growth factors and/or related morphogenetic proteins, peptides or other associated molecular components, such binding sequences as can be identified through known phage display processes, including but not limited to those described in the aforementioned co-pending, co-filed applications.

As described more fully below, such epitope sequences arranged and/or configured (e.g., in a further branched or cyclic configuration) as would be known in the art, can be coupled to or bonded directly with the peptide component of an amphiphilic compound of this invention at or about the N-terminus thereof. Whether or not such a residue is of lysine or another such naturally-occurring amino acid, epitope number and identity can be varied depending upon such residues and available, pendant chemical function. Likewise, length or sequence of the peptide component can be varied depending upon desired flexibility, charge and/or capacity for intermolecular attraction or bonding. The hydrophobic component of such compounds can also be varied (e.g., $\sim C_6$-$\sim C_{22}$ alkyl or substituted alkyl, saturated or unsaturated, etc.), limited only by resulting amphiphilic character and affect on associated systems of such compounds.

As described more fully below, the present invention relates to branched peptide amphiphiles (PAs), embodiments of which can self assemble into nanofibers under physiological pH conditions. For example, with the addition of pH 7.4 phosphate buffer and in basic conditions, or otherwise under physiological conditions, such PAs with the branched peptide sequence self-assemble into cylindrical micelles which form self-supporting gel samples. Such PAs with the branched peptide sequence may result in a better exposure of a biologically active peptide sequence on the surfaces of self assembled nanofibers. Peptide amphiphiles having a branched peptide component can also permit presentation of multiple epitopes from a single peptide amphiphile. Examples of such biologically active peptide epitopes include but are not limited to sequences comprising Arg-Gly-Asp-Ser (RGDS)(SEQ ID NO: 1), Pro-His-Ser-Arg-Asn (PHSRN) (SEQ ID NO: 2), Ile-Lys-Val-Ala-Val (IKVAV)(SEQ ID NO: 3), and Tyr-Ile-Gly-Ser-Arg (YIGSR)(SEQ ID NO: 4). Such peptide sequences or epitopes may be used but are not limited to imparting cell adhesion activity or cell receptor binding properties to such compounds or assemblies.

One embodiment of the present invention can comprise a branching peptide amphiphile having an epitope, that when self assembled, places one or more epitopes at the periphery of a nanofiber configuration with synergistic sequence(s) promoting cell adhesion. Another embodiment of the present invention can comprise the presence of more than one biologically functional group on a branched PA compound. Without restriction to any one theory, it is believed that branching permits better access and presentation of the group(s) and/or epitope(s) on the surfaces of an assembly thereof.

Another embodiment of this invention can comprise a treatment method comprising cellular administration of any of the present peptide amphiphiles for purpose of but not limited to tissue repair or bone growth. In certain embodiments, the peptide amphiphiles self assemble before administration, or self assemble upon or after cellular contact or administration to a cellular environment. Without limitation, self assembled nanofibers which comprise the peptide amphiphile with the branched peptide portion may also comprise cells or a therapeutic agent or composition in association with the hydrophobic component of a micelle or one or more epitopes on the surface of the micelle which may be delivered as part of a therapy to a cell sample or to a mammalian/patient cellular or tissue site. Such embodiments can encapsulate, have bonded to their epitopes or otherwise present various cells and or therapeutic agents such as but not limited to anti-inflammatory compounds, chemotherapeutic compounds, and combinations of these.

The peptide amphiphiles including the branched peptide sequence can be used in a medical applications with different epitopes chosen according to their desired functions. Self assembled materials made from these peptide amphiphiles may be used as a scaffolding for tissue transplant, reconstructive tissue growth, or tissue growth in vitro or in vivo. The amphiphilic character of the peptide amphiphiles with the branched peptide sequence can be used to encapsulate hydrophobic drugs in the core of nanofibers. In addition, representing use of a spectroscopic probe, a Gd complexing DOTA molecule may be attached as one of the epitopes of the nanofibers for magnetic resonance imaging studies of tissues or cells in vitro or in vivo.

BRIEF DESCRIPTION OF THE DRAWINGS

In part, other aspects, features, benefits and advantages of the embodiments of the present invention will be apparent with regard to the following description, appended claims and accompanying drawings where:

DETAILED DESCRIPTION OF CERTAIN EMBODIMENTS

Embodiments of the present invention include peptide amphiphiles with a branched peptide sequence which may self assemble to form micelles. Such micelles include but not limited to cylindrical fibers or nanofibers. Although the self assembled structures disclosed herein are nanofibers, the present invention includes any self assembled structure and the present invention is not limited to nanofibers.

In the present invention, the peptide amphiphiles can have more than one branch to which various groups can be coupled or chemically bonded. These groups or epitopes can be biologically active and can include but are not limited to amino acids, a cell adhesion peptide sequence, peptides, peptide and protein sequences derived from a phage display process, a fluorescent probe, a radiological probe, a magnetic probe, and combinations of these. As illustrated by example only in FIGS. 1-4, peptide amphiphiles with a branched peptide component can include but are not limited to: those with one or more peptides or amino acid residues (e.g., PA6) linked to a branching amino acid such but not limited to as lysine (K); those with an epitope and a side chain peptide or amino acid residue (e.g., PAs 1, 4 and 7) linked to a branching amino acid such but not limited to as lysine (K); those with two or more of the same epitope (e.g., PA2) linked to a branching amino acid such but not limited to as lysine (K); and those with multiple epitopes (e.g., PAs 3 and 5) linked to a branching amino acid such but not limited to as lysine (K).

Figure 4:
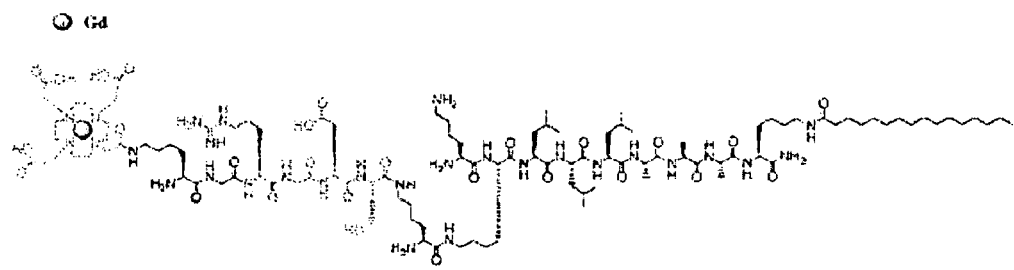
Figure 5:
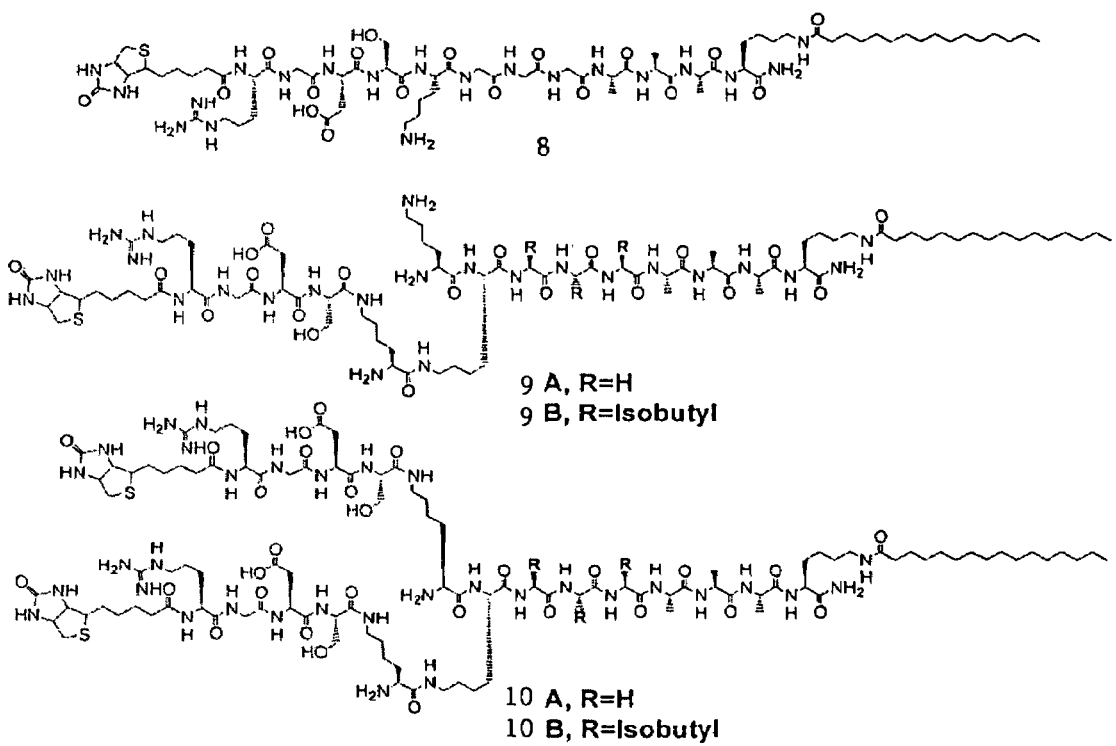
FIG. 5 provides amphiphile structures 8-10.

By way of example only, the peptide amphiphile (7) of the present invention has a hydrophobic component, which can be a $C_{16}$ alkyl chain, and a branched peptide component. The peptide component comprises the branching amino acid residue lysine (K) and the epitope (DOTA-KG-RGDS-K) (SEQ ID NO: 5) as shown in FIG. 4 vide infra.

In PA7, the peptide component (K-LLL-AAA-(K)) (SEQ ID NO: 6) is coupled toward the C-terminus with lysine to the hydrophobic component. The peptide component can have at least two components non-linear thereto via a branching amino acid (e.g., K). One or both of peptide branches can include a biologically active epitope such as but is not limited to amino acids, a cell adhesion sequence, a peptide, peptide and protein sequences derived from a phage display process, a fluorescent probe, a magnetic probe or combinations of these.

The presence of peptide amphiphiles with a branched peptide sequences in self assembled nanofibers may offer better exposure, accessibility, or availability of the epitopes on the branched peptide to external molecules. This accessibility can have important benefits for biomedical applications such as but not limited to tissue regeneration, scaffolds for tissue transplants, cell recognition, and reconstructive surgeries.

Presentation of a single RGDS (SEQ ID NO: 1) sequence in a branching peptide (1) of the present invention is a non-limiting example of biologically active peptide amphiphiles of the present invention which are designed to be a more readily recognized epitope at the periphery of nanofibers self assembled from them. A linear PA of the prior art can contain only one epitope. In the branched systems of the present invention, more than one epitope can be used to improve biological activity. For this purpose, synergistic sequences of cell adhesive epitopes may also be synthesized on the same PA, as shown for example by (PA3) in FIG. 1 and by PA5 in FIG. 2. Currently, addition of ions or changing the pH to acidic or basic conditions are methods used to form the traditional PA nanofibers. The branched PAs of the present invention advantageously form nanofibers and self-supporting gels at neutral pH and under basic conditions. Nanofiber formation at physiological pH is a desirable property for most of the biological applications of such peptide amphiphiles. Multiple functional groups can be attached to these branched PAs via solid phase synthesis. Fluorescent probes can be attached to the free amine groups of lysine amino acids. Also the free amine group at the hydrophilic surface of nanofibers made from peptide amphiphiles of the present invention would be available for other ion sensing probes. The DOTA branched PA7 is but one example of this type of peptide amphiphile compound. The Gd complexing DOTA moiety on branched PA7 may be useful relaxation studies for magnetic resonance imaging applications.

Various agents or reagents may be used to self assemble the peptide amphiphile of the present invention. Such agents may include but are not limited to complementarily charges peptide amphiphiles, acids or bases, multivalent ions, dehydration and combinations of these. Preferably the branched PAs of the present invention form nanofibers and self-supporting gels at, or upon achieving physiological pH or basic conditions.

Figure 1:
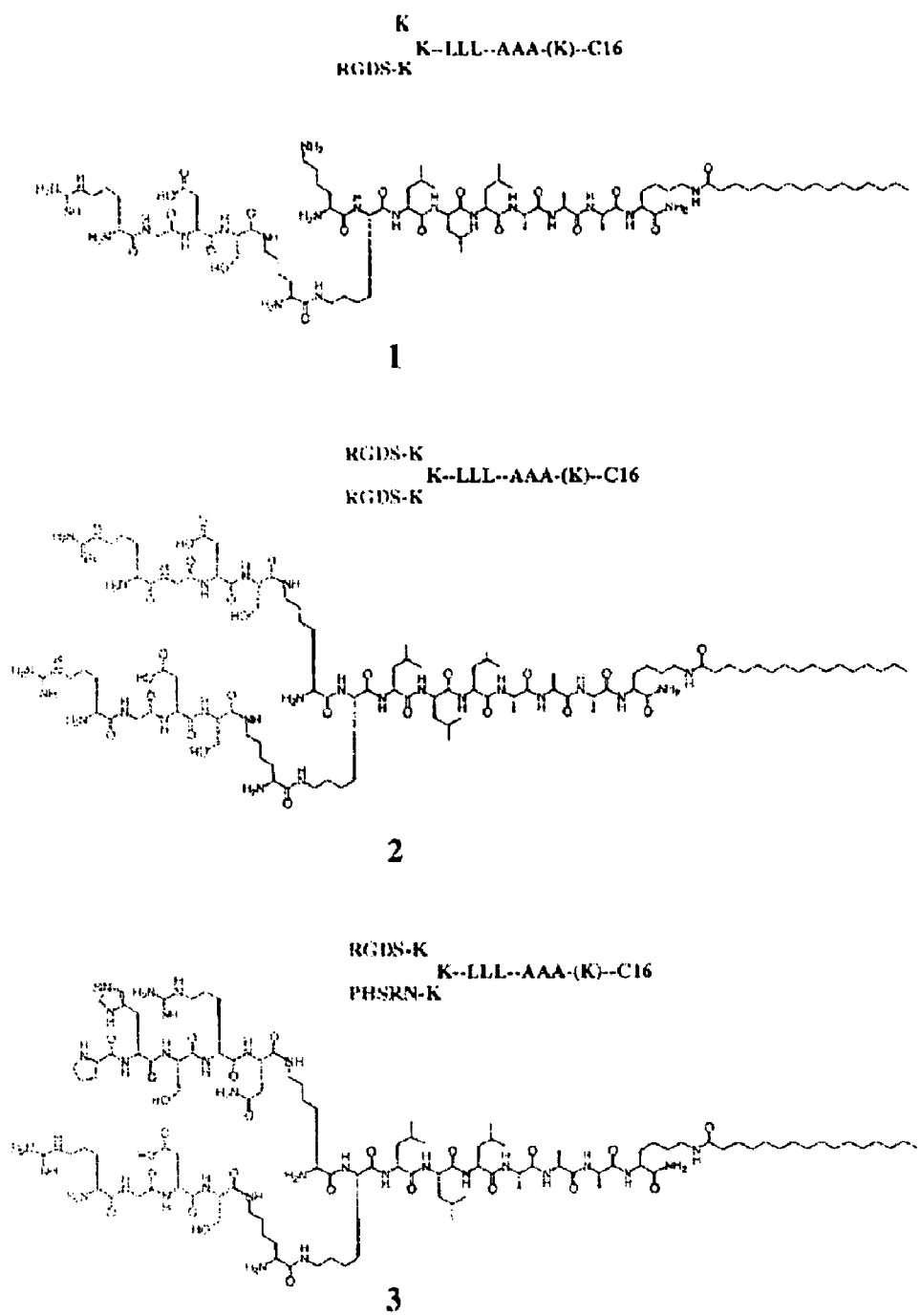
FIG. 1 includes illustrations of the molecular structures of peptide amphiphiles (1), (2), and (3) of the present invention.
Figure 2:
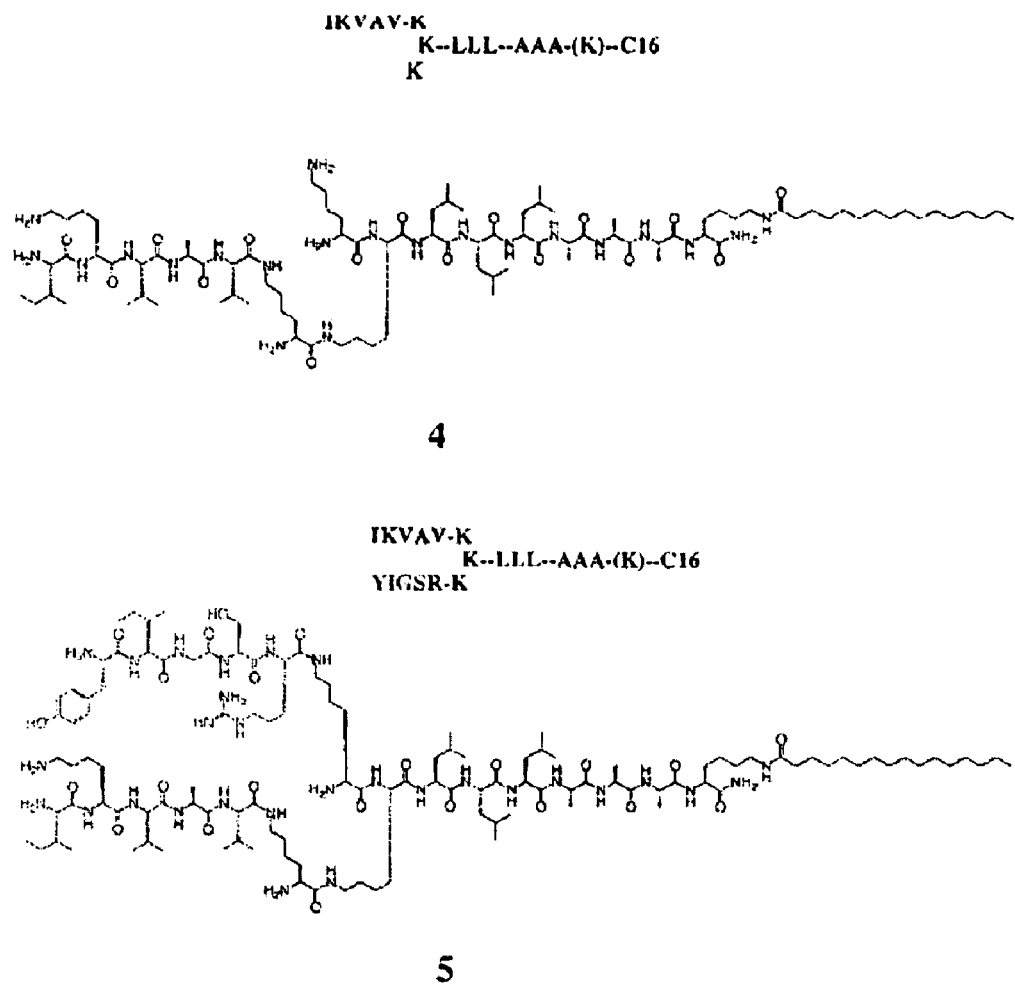
FIG. 2 includes illustrations of the molecular structures of peptide amphiphiles (4) and (5) of the present invention.

Amino acids having pendent amino groups useful for coupling to other peptides can be used to synthesize the branched structure of the peptide amphiphiles of the present invention. One or more such residues can be incorporated into the peptide component to create multiple branching sites. Peptide amphiphile 1 in FIG. 1 has branching amino acid lysine on the backbone of the peptide amphiphile which forms a branch to an RGDS-K (SEQ ID NO: 7) epitope and another lysine amino acid (K–). Where more than one branch is desired, multiple amino acids, each with a pendent side chain and/or amino group may be used as illustrated in FIG. 1 for peptide amphiphile (2). Lysine may be used to synthesize branches of the peptide amphiphiles in the present invention because it has two functional amine groups which may be used to modify its chemistry. However, the present invention is not limited to lysine, and other amino acids with two or more functional groups which may be converted to amines or other useful functionalities for solid phase synthesis of peptides may be used for the branching amino acid. For example, amino acid with amine side chains including but not limited to naturally occurring amino acids and non-naturally occurring amino acids such as beta or gamma amino acid may be used. Preferably the branching amino acids are chosen such that they can that can be modified to form at least alpha and epsilon amine side groups. These alpha and epsilon amine side groups can be used to continue peptide synthesis of the branches. Orthogonal protecting groups can be used on the one or more amine side groups to enable different chemistry to be performed on them independently. For example, to attach the hydrophobic component, the orthogonal protecting group strategy may be used without harming the alpha amine protection. In this case, the epsilon amine protection may be removed and the alkyl chain coupled to the deprotected amino acid.

Branching may be increased by using multiples of a chosen branching amino acid. For example, one branching lysine can provide 2 active branching sites, an additional 2 lysines can provide 4 active branching sites, and an additional 4 lysines can provide 8 active branching sites.

Alpha and epsilon amine protection of the lysine residue(s) was selected according to the branch design. If two different branches are desired, Mtt group was used for lysine side chain protection. For growing the first branch, Fmoc group was removed without removing Mtt protection. After completion of the first branch sequence, the last amino acid was selected with a Boc protection which is resistant to the Mtt cleaving conditions. Mtt is then removed to grow the second branch of the PA. If two similar branches was desired, Fmoc side chain protected lysine was used to make the PA. Both Fmoc groups were removed by piperidine solution, and the two branches of the PA were made at the same time.

Figure 3:
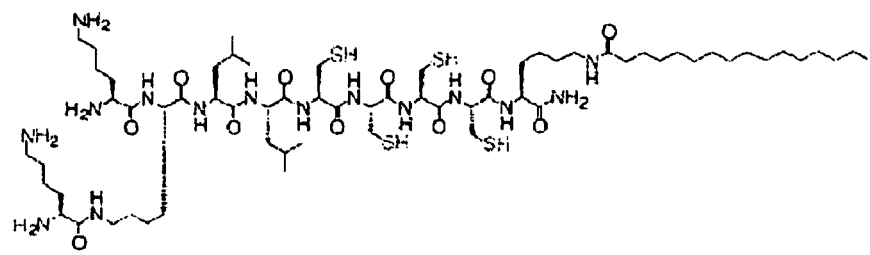
FIGS. 3-4 includes illustrations of the molecular structures of peptide amphiphiles (6) and (7) of the present invention.

The branched PAs and self assembled micelles thereof can be used in tissue engineering, tissue reconstruction, synthetic vaccine design, drug delivery, magnetic resonance imaging and sensor applications. The amphiphilic character of these PAs can also be used to isolate single walled carbon nanotubes. For example, branched PA6, as shown in FIG. 3, can be used to encapsulate hydrophobic drug or other therapeutic molecules. The self assembled nanofibers which includes the peptide amphiphile with the branched peptide portion may also include cells or a therapeutic composition at the core of the micelle or coupled to one or more epitopes on the surface of the micelle which may be delivered as part of a therapy to a cell sample or to a site on a patient that includes cells or tissue. Where the nanofibers are in the form of a pre-molded or pre-formed scaffold, the nanofibers may encapsulate or have bonded to their epitopes various cells and or a therapeutic composition such as but not limited to anti-inflammatory compounds, chemotherapeutic compounds, and combinations of these which may be delivered as part of a therapy to a cell sample or to a site on a patient that includes cells or tissue.

The PA compounds of the present invention can generally comprise, in certain embodiments, a hydrophobic alkyl component and a branched peptide component. The branched peptide component can comprise charged groups, epitopes, and biological signals by virtue of the arrangement and choice of the amino acid residues in the component. Hydrophilic amino acids may be charged and can be used to provide a degree of solubility in an aqueous environment. In an aqueous environment, such peptide amphiphiles have the ability to self-assemble into cylindrical micelles or nanofibers with the hydrophobic components tails oriented toward the center and with the generally hydrophilic functional peptide branched peptide exposed along the peripheral surface. The branched peptide component, is bulky relative to the hydrophobic component, giving the PA compound an overall conical shape. While not wishing to be bound by theory, it is thought that this shape as well as the hydrophobic and hydrophilic arrangement of the segments plays a critical role in PA self-assembly. With the branched peptide groups exposed along the length of the fiber, a bioactive epitope or biological signal can be presented to the environment.

To enhance the robustness of a PA compound, the peptide component can comprise one or more cysteine residues as shown in PA (6) in FIG. 3, coupled to a lysine amino acid (as shown) or other amino acids such as but not limited to alanine and or glycine. When assembled, the S—H ligands of neighboring cysteine residues are in close enough proximity to allow stable disulfide bond formation; exposure to oxidative conditions such as iodine or oxygen leads to disulfide bond formation and cross-linking of the fibers. One versatile feature of such PAs is reversible cross-linking. The PA fibers can be disassembled using a reducing agent such as dithiolthreitol (DTT). The PA can otherwise be self-assembled, improving its adaptability for medical use.

The hydrophobic component can be a hydrocarbon, such as but not limited to an alkyl moiety or other structure which can be used to provide amphiphile function. The size of such a moiety may be varied, but in certain embodiments range from about and greater than $C_6$ in length. This component of the peptide amphiphile serves to create the slender portion of the PA molecule's conical molecular shape. Other chemical groups, such as triacetylenes, which provide hydrophobicity and a shape which allows self assembly to the peptide amphiphile may also be used. The hydrophobic component is covalently coupled or bonded to the peptide component, as described above.

The peptide component of the branched PA compound component can comprise, as discussed above, cysteine residues, if cross-linking is desired. Regardless, other amino acids such as but not limited to alanine, serine, or leucine may be used in this region (e.g. SLSL (SEQ ID NO: 8) or AAAA (SEQ ID NO: 9) as described in more detail herein). Such cysteine-free components may be more appropriate for in situ biological applications where the environment may be more difficult to regulate cross-linking. The SLSL (SEQ ID NO: 8) modification to the system is expected to lead to a slower assembly of the nanofibers. Without wishing to be bound by theory, it is believed that the bulky leucine side chains may require more time to pack into the fiber. A slowed self-assembly may also have greater applications in a functional, in situ environment such as an operating room, where it may be advantageous to have delayed formation of the nano-fibers. The peptide component can also include residues such as but not limited to glycine to impart structural flexibility.

The peptide component can comprise any naturally or non-naturally occurring amino acid, including but not limited to a charged or hydrophilic amino acid such as lysine, serine, phosphorylated serine, diaminopropionic acid, diaminobutyric acid, and aspartic acid—the choice of which can provide a charged peptide-amphiphile, such as PA6 shown in FIG. 3. Near physiological pH, such charged peptide-amphiphiles may be positively or negatively charged. The peptide component is a relatively bulky, charged segment of the PA compound, providing, with one or more branches, the widest region of the conical molecular geometry.

Self-assembly of mixtures of different PA compounds can also allow for the presentation of different amino acid sequences along the length of an assembled nanofiber of corresponding peptide components of varying length and/or amino acid sequence. Further, it is contemplated that self assembly of branched peptide amphiphiles of different sizes, or mixtures of branched peptide amphiphiles and filler peptide amphiphiles of different sizes, or combinations of these may be self assembled from nanofibers or other micelles having protruding peptide amphiphiles on the surfaces of the self assembled nanofibers or micelles.

Various peptide amphiphile compounds and the branched PAs of the present invention can be synthesized using preparatory techniques well-known to those skilled in the art, including those disclosed in the aforementioned co-pending published application and co-pending application Ser. No. 10/294,114 filed Nov. 14, 2002 (International publication no. WO 03/054146), the contents of which are incorporated herein by reference in their entirety, and modifications of those techniques originally described by Stupp et al. (See e.g., J. D. Hartgerink, E. Beniash and S. I. Stupp, *Science* 294, 1683-1688, 2001), which is also incorporated in its entirety by reference. The synthetic schemes set forth in these references may be applied to the present invention. Peptide amphiphiles may be in their fully protonated form, partially protonated form, or as acid or basic addition salts. Generally such peptide amphiphiles can be made by standard solid-phase peptide chemistry including addition of a hydrophobic tail at or near the N-terminus of the peptide. Modifications of these synthetic methods can be made as would be known to those skilled in the art and aware thereof, using known procedures and synthetic techniques or straight-forward modifications thereof depending upon a desired amphiphile composition or peptide sequence. For example the hydrophobic tail is bonded to the amine group on the pendent chain of the lysine amino acid rather than the amine group on the chiral carbon.

EXAMPLES OF THE INVENTION

The following non-limiting examples and data illustrate various aspects and features relating to the compounds, systems and/or methods of the present invention, including the self-assembly of various branched peptide amphiphile compounds having associated therewith one or more bioactive epitope sequences, such compounds as are available through the synthetic methodology described herein and through those co-pending applications incorporated by reference. In comparison with the prior art, the present compounds, systems and/or methods provide results and data which are surprising, unexpected and contrary thereto. While the utility of this invention is illustrated through the use of several amphiphilic peptide compounds, branched configurations and/or epitope sequences which can be used therewith, it will be understood by those skilled in the art that comparable results are obtainable with various other peptide compounds, and epitopes coupled thereto, as are commensurate with the scope of this invention.

Example 1

This example describes the preparation of peptide amphiphiles which include a branched peptide segment. (Reference is made to the aforementioned incorporated applications, and the synthetic detail provided therewith, in conjunction with FIGS. 6 and 7, below.) All of the peptides were synthesized by Fmoc Solid Phase Peptide Syntheses (Fmoc SPPS) protocol. Fmoc, Boc and 4-Methyltrityl (Mtt) protected amino acids, MBHA Rink Amide resin, and HBTU were purchased from NovaBiochem. The other chemicals were purchased from Fischer or Aldrich and used as provided. Peptides were constructed on MBHA Rink Amide resin. Amino acid couplings were performed with 4 equivalents of Fmoc protected amino acid, 3.95 equivalents HBTU and 6 equivalents DIEA for 4 h.

Fmoc deprotections were performed with 30% Piperidine/DMF solution for 10 min. Mtt removal was done with 1% TFA/Dichloromethane solution in the presence of TIS for 5 min. Cleavage of the peptides from the resin was carried out with a mixture of TFA:TIS in ratio of 97.5:2.5 for 3 h. The excess TFA was removed by rotary evaporation. The remaining viscous peptide solution was triturated with cold ether and the resulting white product was dried under vacuum. PA's were characterized by Matrix Assisted Laser Desorption Ionization-Time of Flight Mass Spectrometry (MALDI-TOF MS) and/or Electrospray Ionization Mass Spectrometry (ESI-MS).

Transmission Electron Microscopy (TEM) samples were prepared with 1 wt % gels of the PA's on a holey carbon coated TEM grid. Negative staining was done by 2% phosphotungstic acid solution. One wt % gels of PA's for TEM were prepared by mixing one to one 2 wt % PA solution in water and phosphate buffer (pH=7.4).

Initially, resin was swelled in DMF for 30 min and then Fmoc protecting group on the resin was removed by 30% Piperidine/DMF solution. Then Fmoc-Lys (Mtt)-OH was coupled to the resin. Lysine side chain protecting group, Mtt, was removed by 1% TFA/Dichloromethane solution without cleaving Fmoc protection. Palmitic acid ($C_{16}$ alkyl chain) was coupled to the resin with amino acid coupling reagents. After completion of the palmitic acid coupling, Fmoc was removed by piperidine solution and amino acids which are the rod part of the PA were coupled in the same way (Fmoc SPPS).

Lysine was chosen to synthesize branches of the PA. Alpha and epsilon amine protection of the lysine was selected according to the branch design. If two different branches are desired, Mtt group was used for lysine side chain protection. For growing the first branch, Fmoc group was removed without removing Mtt protection. After completion of the first branch sequence, the last amino acid was selected with a Boc protection which is resistant to the Mtt cleaving conditions. Then Mtt is removed to grow the second branch of the PA. If two similar branches was desired, Fmoc side chain protected lysine was used to make the PA. Both Fmoc groups were removed by piperidine solution, and the two branches of the PA were made at the same time.

Example 2

The series of molecules described below illustrates a novel branched PA architecture, designed to increase the accessibility of epitopes to receptors on nanofiber surfaces by using a bulky, sterically hindered peptide structure. The representative, non-limiting molecules contain lysine dendron moieties, and similar to other linear PAs of the type incorporated herein, self-assemble to form aqueous gels formed by a network of nanofibers. As shown in FIG. 5, the molecules contain the peptide sequence KXXXAAAK (SEQ ID NO: 10) (X=G or L) followed by a saturated sixteen-carbon alkyl segment, with the dendron branch introduced at a lysine residue. Alanine, glycine and leucine residues were used to promote hydrogen-bonded β-sheet formation, which should favor aggregation into extended structures such as cylindrical nanofibers, rather than into spherical micelles as is more typically observed in amphiphilic self-assembly. The well known biological epitope RGDS (SEQ ID NO: 1) is present in cell binding domains of extracellular proteins such as fibronectin and vitronectin, and was used to illustrate incorporation of one or more of a range of bioactive peptides into such PA systems. The RGDS (SEQ ID NO: 1) epitope is known to bind to integrin receptors, and this molecular recognition event plays a critical role in adhesion of cells to the extracellular matrix and in the complex cascade of signaling that follows.

Molecule 8 was synthesized with a linear peptide structure to compare epitope availability with that in branched PAs of this invention. A lysine residue was introduced to create asymmetrically branched molecules 9A and 9B, thereby altering structural presentation of the bioactive peptide sequence after self-assembly. Molecules 10A and 10B were synthesized to introduce symmetrical branches in a similar fashion to 9A and 9B, and to investigate the presentation of multiple epitopes by a single PA molecule. Furthermore, in molecules 9 and 10, the effect of hydrophobic side chains on structural accessibility of the epitope was studied by exchanging glycine (R=H) residues with leucine (R=isobutyl) residues. To examine recognition and availability of epitopes, the RGDS (SEQ ID NO: 1) sequence on each PA was terminated with a biotin group, and biotin accessibility was then probed using the binding of a fluorescein isothiocyanate (FITC)-labeled avidin molecule. It is well known that avidin has a very high affinity for biotin, with four biotin binding sites per protein. This binding affinity has been previously used to study surface availability of monolayers by varying the number of biotin moieties presented. Interactions between the fluorophore and amino acid residues in the biotin binding site of the avidin cause quenching of fluorescence. Therefore, binding of the biotinylated PA with fluorescently labeled avidin should lead to a significant fluorescence recovery by weakening the quenching interactions.

Example 3

The branched PAs were prepared using solid phase peptide synthesis (SPPS). Branching of the peptide segment was achieved by using orthogonal protecting group chemistry. (See, Bourel, L.; Carion, O.; Masse, H. G.; Melnyk, *O. J. Peptide Sci.* 2000, 45,488-496; and Aletras, A.; Barbs, K.; Gatos, D. Koutsogianni, S.; Mamos, P. *J. Peptide Protein Res.* 1995, 6, 264-270.) Fmoc, Boc and 4-methyl trityl (Mtt) protecting groups on the amines of the lysine residues were used to control the design of peptides, as each of these protecting groups can be manipulated independently. Fmoc protected amines were used to couple amino acids onto the peptide, Boc protecting groups were used to block lysine branches, and Mtt was used for selective deprotection and growth of asymmetrical branches. The RGDS (SEQ ID NO: 1) epitope was coupled to the ϵ amine of the lysine residue to enhance the epitope's conformational freedom, due to the flexible four-carbon linker. Biotinylation of the PAs was achieved via SPPS by coupling a biotin to the end of the peptide sequence.

Example 4

All PAs were soluble in water at pH 4 and formed self-supporting gels at concentrations greater than 0.5 wt % when pH was increased above about 6.5. Gel formation was found to be fully reversible with pH change. Transmission electron microscopy (TEM), atomic force microscopy (AFM), FT-IR and circular dichroism (CD) spectroscopy were used to characterize the self-assembly of branched PA molecules. TEM micrographs of self-assembled PAs 8-10 at pH 7.4 revealed the formation of uniform, high aspect ratio nanostructures with diameters of 7±1 nm and ranging from hundreds of nanometers to several micrometers in length. The FT-IR of lyophilized (freeze-dried) gels of all PAs indicates hydrogen bonding between the peptides, based on N—H stretching peaks at 3280-3285 $cm^{-1}$. Amide I peaks at 1628-1632 $cm^{-1}$ are consistent with a predominantly β-sheet-like character for the peptide secondary structure, with some α-helix and random coil conformations, indicated by peaks in the range of 1650-1675 $cm^{-1}$. Additionally, a shift of $\nu_a$ ($CH_2$) from ca. 2932 to ca. 2921 $cm^{-1}$ indicates a high degree of ordering in the palmityl hydrophobic segment. Circular dichroism spectra from the self-assembled PAs reveals a broad peak (nπ* transition) between 200 and 230 nm which can be interpreted as a signature for the predominant presence of β-sheets, as well as minor contributions from α-helical and random coil conformations. IR and CD results are consistent with a highly ordered assembly of hydrogen bonded PAs with β-sheet character, resulting in densely packed molecules within the nanofibers.

Example 5

Dilute samples of biotinylated PAs were prepared at pH 7.4 to investigate the influence of binding with FITC-avidin. Interestingly, a significant increase in fluorescence emission is observed upon binding of FITC-avidin to biotinylated branched PAs, relative to linear PA 8. This result suggests that, despite the structural similarity observed by TEM, FITC-avidin has greater accessibility to the biotin on the surface of nanofibers made up of branched molecules compared with those made up of linear molecules. In linear PA systems, dense hydrogen bonding may result in more compact packing of the epitopes on the surface of nanofibers, thus hindering binding of FITC-avidin to biotin, resulting in less recovery of fluorescence emission. However in the sterically hindered branched systems, enhanced availability of biotin to the avidin receptor may indicate less effective packing of molecules on the fiber surface. In addition, incorporation of hydrophobic side chains on the PA structure altered the availability of the epitopes as well. Biotin availability on 9B and 10B was significantly higher than on 9A and 10A, respectively. Therefore, hydrophobic side chains in these molecules may also be affecting the nature of packing in the assembly and consequently epitope availability.

Example 6

As a control, non-biotinylated versions of PA 8 and 9B were prepared and tested with FITC-avidin under the same conditions. No significant change in the fluorescence of FITC-avidin was observed, indicating that the increased fluorescence is not due to non-specific avidin binding to the PA. These results confirm the proposed effect of branching and hydrophobic side chains on epitope availability at the periphery of the nanofibers. Biological experiments are underway to establish if structural differences in RGDS (SEQ ID NO: 1) epitope presentation on the nanofibers influences in similar fashion the more complex recognition process of this peptide sequence by cells cultured with the peptide amphiphile nanofibers.

Example 7

Figure 6:
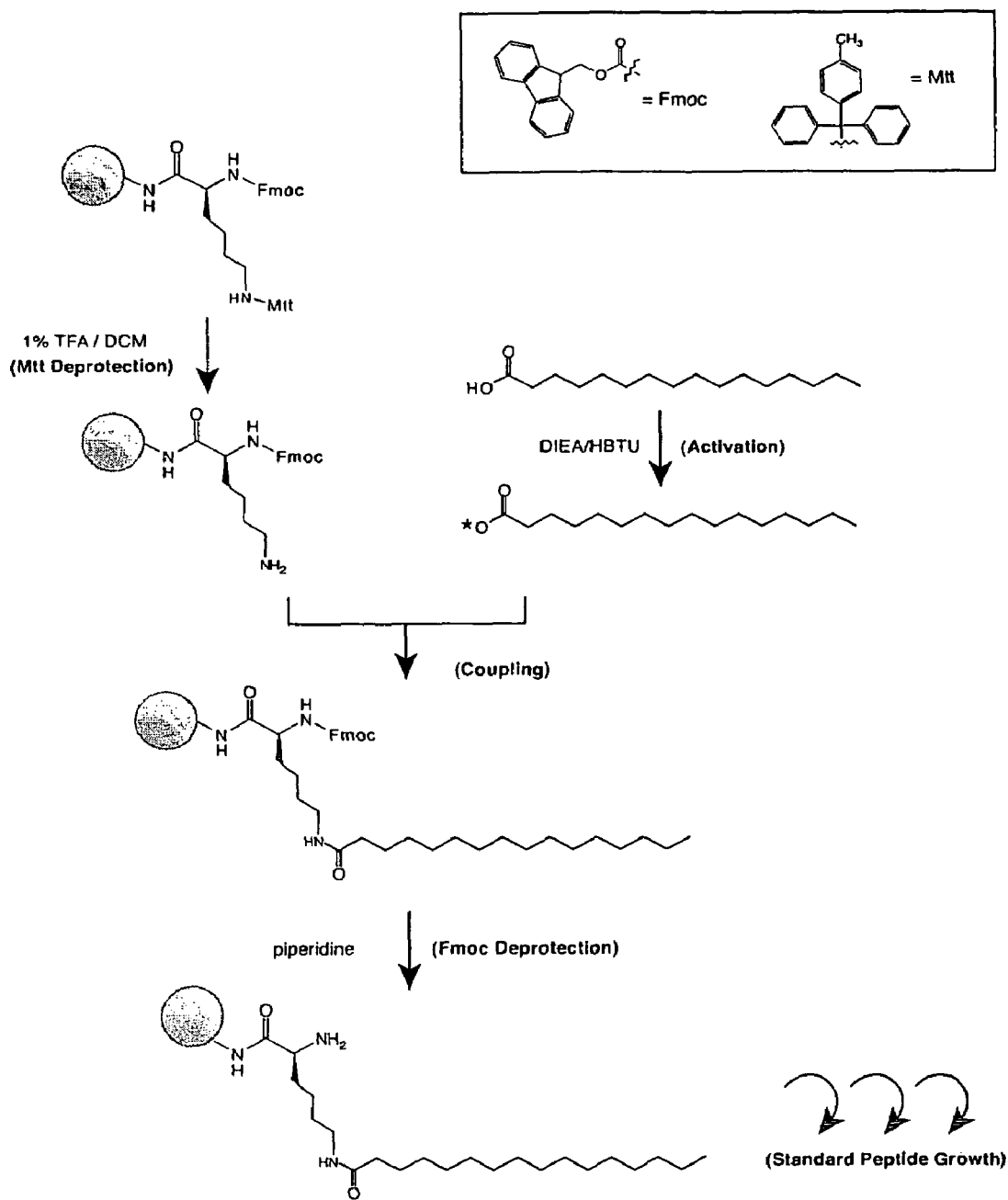
FIGS. 6-7 schematically illustrate synthesis of representative peptide amphiphile compounds. Non-branched peptides in FIG. 7 are disclosed as SEQ ID NOS 12-14 respectively in order of appearance.
Figure 7:
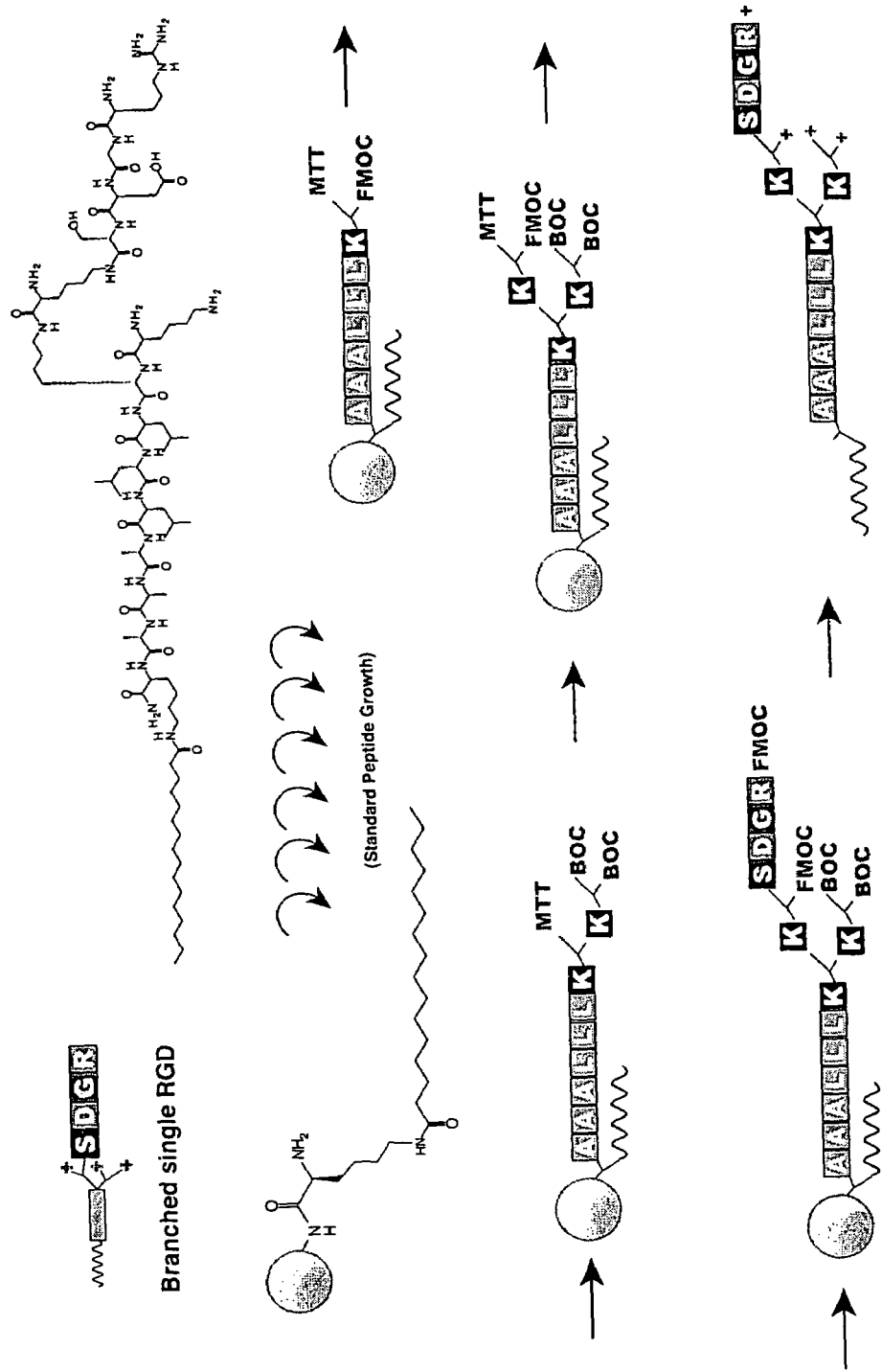

As described and as provided in the aforementioned incorporated references, the peptide amphiphile compounds of this invention can be prepared so as to provide a structural polarity reversed according to convention. By comparison, solid phase synthesis typically requires that peptide segments be synthesized from the C-terminus to the N-terminus. As a result, such amphiphilic compounds have been prepared by capping the free N-terminus with an alkyl moiety, resulting in a compound with either a free acid or amide group at the C-terminus. Here, in contrast, for purposes relating to bioactivity or synthetic flexibility, it can be desirable to provide a peptide amphiphile with a free N-terminus. Accordingly, a synthetic route was devised to allow introduction of a hydrophobic component on or about the C-terminus, and provide one or more pendant functional groups to effect branching and epitope coupling. FIGS. 6 and 7 schematically illustrate such synthetic modifications. With reference to FIG. 6, the hydrophobic component (e.g., an alkyl moiety) is added before peptide growth, using orthogonal protecting groups. With reference to FIG. 7, corresponding protection/deprotection strategies allow for creation of branching at one or more lysine residues, as well as selective epitope (e.g., RGDS) (SEQ ID NO: 1) coupling, providing amine termination at the peptide periphery of a corresponding micellar configuration.

As the preceding illustrates, cylindrical nanostructures formed by branched peptide amphiphile molecules present high densities of surface binding sites. The branched covalent architecture of such molecules leads to greater accessibility of binding sites to a probing protein receptor, an observation useful in supramolecular design of bioactivity in synthetic nanoscale materials for biology and medicine.

---

We claim:

1. A non-linear peptide amphiphile compound comprising a peptide component having the formula KXXXAAAK (SEQ ID NO: 10), wherein X is G or L, which peptide component further has at least one pendant lysine residue coupled to a component non-linear with said peptide component, wherein the component non-linear with said peptide component is selected from IKVAV (SEQ ID NO: 3), YIGSR (SEQ ID NO: 4), RGDS (SEQ ID NO: 1), and PHSRN (SEQ ID NO: 2), wherein said peptide component is coupled to a hydrophobic component, and wherein the hydrophobic component is an alkyl moiety ranging from $C_6$-$C_{22}$.

2. The compound of claim 1 wherein X is L.

3. The compound of claim 2 wherein IKVAV (SEQ ID NO: 3) and YIGSR (SEQ ID NO: 4) are non-linear to said peptide component.

4. The compound of claim 3 wherein said compound has the following formula:

IKVAVK
    KLLLAAAK$C_{16}$
YIGSRK.

5. The compound of claim 1 wherein each of said two lysine residues is coupled to one of said epitope sequences.

6. The compound of claim 5 wherein at least one of said sequences is coupled to a spectroscopic probe component.

7. The compound of claim 1 assembled into a micellar configuration.

8. A system comprising a non-linear peptide amphiphile compound comprising a peptide component, a hydrophobic component coupled to said peptide component at its N-terminus, said peptide component comprising a peptide of the formula KXXXAAAK (SEQ ID NO: 11), wherein X is L or K, further comprising at least one pendant lysine residue which is coupled to a sequence selected from IKVAV (SEQ ID NO: 3), YIGSR (SEQ ID NO: 4), RGDS (SEQ ID NO: 1), and PHSRN (SEQ ID NO: 2), wherein the hydrophobic component is an alkyl moiety ranging from $C_6$-$C_{22}$, and wherein said compound is in a fluid medium.

9. The system of claim 8 wherein X is L.

10. The system of claim 9 wherein said compound comprises IKVAV (SEQ ID NO: 3) and YIGSR (SEQ ID NO: 4).

11. The system of claim 8 wherein the compound has the following formula:

IKVAVK
    KLLLAAAK$C_{16}$
YIGSRK.

12. The system of claim 8 wherein said medium is at a physiological pH, said system comprising an assembly of said compounds.

13. A method of using a pendant lysine residue of a peptide amphiphile to present a biologically active epitope sequence, said method comprising: providing a plurality of peptide amphiphile compounds, each of said compounds comprising a peptide component having the formula KXXXAAAK (SEQ ID NO:10), wherein X is G or L, and a hydrophobic component selected from an alkyl moiety ranging from $C_6$-$C_{22}$, at least one of said compounds comprising at least one pendant lysine residue; and coupling a biologically active epitope sequence selected from IKVAV (SEQ ID NO:3), YIGSR (SEQ ID NO:4), RGDS (SEQ ID NO:1), PHSRN (SEQ ID NO:2) to said pendant lysine residue, wherein said epitope sequence is non-linear to said peptide component.

14. The method of claim 13 wherein said epitope sequence further includes the recognition product of a phage display process.

15. The method of claim 13 wherein the N-terminus of said peptide component comprises two lysine residues.

16. The method of claim 15 wherein each of said lysine residues is coupled to an epitope sequence selected from RDGS (SEQ ID NO: 1), PHSRN (SEQ ID NO: 2), IKVAV (SEQ ID NO: 3), YIGSR (SEQ ID NO: 4) and the recognition product of a phage display process.

17. The method of claim 13 wherein said compounds are in an aqueous medium, and the pH of said medium is adjusted to assemble said compounds in a cylindrical micelle.

18. The method of claim 13 wherein at least one of said compounds comprises a peptide component comprising at least two lysine residues.

19. The method of claim 18 wherein each of said residues is coupled to an epitope sequence selected from RGDS (SEQ ID NO: 1), PHSRN (SEQ ID NO: 2), IKVAV (SEQ ID NO: 3), YIGSR (SEQ ID NO: 4) and the recognition product of a phage display process.

20. The method of claim 19 wherein one of said residues is coupled to an RGDS (SEQ ID NO: 1) epitope and one of said residues is coupled to a PHSRN (SEQ ID NO: 2) epitope.

21. The method of claim 20 wherein said compounds are in an aqueous medium and assembled using a reagent in said medium.

* * * * *

UNITED STATES PATENT AND TRADEMARK OFFICE
CERTIFICATE OF CORRECTION

| | | |
|---|---|---|
| PATENT NO. | : 7,452,679 B2 | Page 1 of 1 |
| APPLICATION NO. | : 11/005314 | |
| DATED | : November 18, 2008 | |
| INVENTOR(S) | : Samuel I. Stupp et al. | |

It is certified that error appears in the above-identified patent and that said Letters Patent is hereby corrected as shown below:

In column 1, line 9, please change "DE-FG02-00ER54810" to --DE-FG02-00ER45810--.

In column 10, line 39, please change "pII" to --pH--.

In column 17, claim 1, line 29, please change "PIISRN" to --PHSRN--.

Signed and Sealed this

Fourteenth Day of April, 2009

JOHN DOLL
*Acting Director of the United States Patent and Trademark Office*